United States Patent [19]

Cruz, Jr. et al.

[11] 4,016,877

[45] Apr. 12, 1977

[54] FIBROUS COLLAGEN DERIVED WEB HAVING HEMOSTATIC AND WOUND SEALING PROPERTIES

[75] Inventors: Mamerto M. Cruz, Jr., Pennington, N.J.; John H. Tenery, Fort Worth, Tex.; LaVerne C. Tressler, Trenton, N.J.

[73] Assignee: Avicon, Inc., Fort Worth, Tex.

[22] Filed: Feb. 23, 1976

[21] Appl. No.: 660,065

[52] U.S. Cl. .......................... 128/156; 128/334 R; 128/DIG. 8

[51] Int. Cl.² ....................................... A61L 51/00

[58] Field of Search ................. 128/82.1, 155–157, 128/325, 268, 172.1, DIG. 8, 334 R; 3/1

[56] References Cited

UNITED STATES PATENTS 3,438,374  4/1969  Falb et al. ...................... 128/334 R
3,563,228  2/1971  Seiderman .................... 128/DIG. 8
3,742,955  7/1973  Battista et al. ................. 128/334 R
3,810,473  5/1974  Cruz et al. ..................... 128/334 R
3,892,648  7/1975  Phillips et al. ................ 128/DIG. 8

*Primary Examiner*—Lawrence W. Trapp
*Attorney, Agent, or Firm*—G. F. Mueller; R. D. Jackson; P. Newman

[57] ABSTRACT

Non-woven, liquid-laid, fibrous web having hemostatic and adhesive properties adapted to seal a wound formed of fibers consisting of an ionizable, water-insoluble, partial salt of collagen, the web when placed on a saline solution disintegrating completely and the fibers self disperse. The web is formed from a slurry of the fibers in a water-miscible organic liquid such as ethanol containing a small proportion of an ionizable acid.

9 Claims, No Drawings

FIBROUS COLLAGEN DERIVED WEB HAVING HEMOSTATIC AND WOUND SEALING PROPERTIES

This invention relates to liquid-laid, non-woven sheets or webs particularly suited for medical and surgical purposes consisting essentially of finely-divided fibers derived from collagen.

It has been known that collagen in various treated and prepared forms is useful in medical and surgical procedures and in the treatment of wounds. Collagen in certain forms has hemostatic properties when used as a wound dressing and has a low level of antigenicity. In the U.S. Pat. to Orlando A. Battista, Mamerto M. Cruz, Jr., and Merritt R. Hait, No. 3,742,955 granted July 3, 1973, there is described a fluffy, finely-divided fibrous collagen product derived from natural collagen which when wet with blood has hemostatic properties and a unique adhesive property which is sufficient to join together several biological surfaces. This form of collagen demonstrates an unexpected and entirely unique adhesive property when wet with blood in live warm blooded animals and in many instances can actually be used to adhere severed tissues without the use of sutures.

As described in the aforementioned patent, the hemostatadhesive material is in a fluffy, finely-divided fibrous form and the form for use in the present invention consists essentially of a water-insoluble, ionizable, partial salt of collagen, the fibrous mass having a density of not more than about 8 pounds per cubic foot (0.128 gm./cc.), preferably the bulk density is between 1.5 and 6.0 pounds per cubic foot (0.024 and 0.096 gm./cc.). The mass when combined with blood in a wound forms a mass that is self-adherent to the tissue surfaces and will seal the wound without the use of sutures. The partial salt of collagen consists essentially of an ionizable, water-insoluble, partial acid salt of collagen containing from about 50 to about 90% of the theoretical stoichiometric amount of the ionizable acid. The fluffy, finely-divided fibers for use in the present invention may be prepared as described in the aforementioned patent.

Because of the low density and fluffiness of the product of the aforementioned patent, it is necessary to transfer the product to the wound by the use of forceps or manually with rubber gloves. In such handling procedures fibers become disloged from the bulk being handled and portions will adhere to the forceps or rubber gloves. Although the fluffy, fibrous flour is highly efficaceous as a hemostat-adhesive material, the bulkiness and structureless nature of the product is a decided disadvantage from a handling standpoint and from a standpoint of delivering the product to a wound site.

In the conventional production of water-laid fibrous sheets or webs such as papers, naturally occurring cellulose fibers such as wood pulp and cotton linters are mechanically hydrated as by beating and mixing in a paper mill beater in the presence of a large excess of water. In forming a pulp slurry by a beating operation, the fibers become hydrated and exhibit a microscopic and submicroscopic peeling of individual fibrils along the surface of the fibers and at the end of the fiber bundles. The slurry is then passed to a suitable screen to lay down the fibers as a sheet or mat. The physical properties of the sheet, such as strength, tear and burst are dependent to a large extent on the hydration of the fibers and an interlocking of the hydrated fibers and of the fibrillae on the fibers and the fiber-to-fiber bonding which develops upon drying.

Because of the greater sensitivity to water of the fibers of the fluffy, finely-divided partial salt of collagen having the hemostatic and unique adhesive characteristics as described in the aforementioned patent, water-laid fibrous sheets or webs formed from such fibers are harsh and boardy and parchment-like in structure with complete loss of hemostatic and adhesive properties thereby rendering such sheets unsatisfactory for surgical purposes.

In the U.S. Pat. to Mamerto M. Cruz, Jr., Orlando A. Battista, LaVerne C. Tressler and Carmine Cirolla, No. 3,810,473 granted May 14, 1974, there is disclosed a liquidlaid, non-woven, fibrous web having hemostatic and adhesive properties formed from this fluffy, finely-divided fibrous product.

As disclosed in this latter patent, the production of products having a parchment-like, harsh structure is avoided by slurrying the hemostat-adhesive fibers in a liquid consisting of a mixture having a composition, by volume, in the range of from 95% organic liquid and 5 water to about 85% organic liquid and 15% water. When the organic liquid is ethanol, the mixtures contain, by weight, from 93.73% ethanol and 6.27% water to about 81.69% ethanol and 18.31% water. In the method as disclosed, where the amount of water is less than 5 volumes to 95 volumes (6.27% to 93.73%, by weight) of organic liquid (ethanol) the finished product was unsatisfactory because it is extremely flaky; that is, fibers readily separate from the sheet. Non-woven sheets or webs were prepared from slurries of hemostat-adhesive fibers in 100% ethanol and received high "in vivo" ratings based upon hemostatic efficacy, adhesiveness to wound surfaces and delamination. However, such sheets were unsatisfactory from a handling viewpoint. The cohesiveness was so poor that the sheets were crumbly, tore easily, were difficult to cut and were so delicate that they could not withstand normal shipping and handling. The slightest abrasion results in a loss of fibers from the sheet or web.

The present invention provides a liquid-laid, non-woven web which retains the hemostatic-adhesive properties of the fluffy, fibrous partial salt of collagen.

The present invention also provides a method of forming the liquid-laid, non-woven sheet or web of the fluffy, fibrous collagen derived product which is flexible, non-flaking and possesses sufficient cohesiveness to withstand normal handling in use and in shipping without separation of individual fibers.

Advantages of this invention will become apparent to those skilled in the art from the following description of the method and product.

In accordance with the present invention, liquid-laid, non-woven sheets or webs having highly efficacious hemostatadhesive properties and having required cohesiveness are prepared by slurrying the fluffy fibers of a partial salt of collagen in 100% ethanol to which has been added a small amount of concentrated hydrochloric acid, depositing the fibers to form a sheet or web, uniformly pressing, under limited pressure, the recovered liquid-laid sheet or web and freeze drying the pressed sheet or web. Although 100% ethanol is employed, some moisture will be absorbed by the ethanol from the atmosphere, some water is included upon addition of concentrated hydrochloric acid and some moisture is present in the collagenous fibers. In general, in forming the fiber slurry, the total water content will be about 2 to 5% at most.

The slurrying liquid is prepared by adding approximately 0.3 gm. of 37.5% hydrochloric acid to 13.62 kg. (30 lbs.) of 100% ethanol. The hydrochloric acid thereby adds approximately 0.185 gm. of water. In forming the slurry, as illustrated in the examples hereinafter included, 9.5 gms. of the collagenous fiber are added to 3 liters (2.356 kg.) of the acidified ethanol. The 3 l. of ethanol contains approximately 0.03 gm. of added water. The fiber contains, on an average, approximately 10% by weight, or 0.95 gm., of moisture. Depending upon the relative humidity of the atmosphere in which the operation is conducted and the time required for the operations, the liquid will absorb from about 1% to about 5% by weight of moisture. Such absorption will add from about 23.56 gms. to about 117.8 gms. of water. Thus, the total water content of the slurrying liquid will be from about 24.54 gms. to about 118.78 gms. per 3 liters or about 1.03% to about 5.04 by weight of water. In the normal preparation of webs as described in the examples, requiring about 15 – 25 minutes, the liquid filtrate contained 1.8% by weight of water by analysis.

Although ethanol is used for the preparation of webs for medical and surgical purposes, for other purposes the ethanol may be replaced by other low molecular weight alcohols, ketones and the like such as, for example, methanol, isopropanol, amyl alcohol, methylethyl ketone, acetone, and mixtures of these organic liquids. The use of the organic liquids other than ethanol is feasible. However, where the product is intended for surgical uses it is essential that the product be freed of such other solvent.

The fluffy fibers of the partial salt of collagen, as described in the aforementioned patents, can be prepared from any undenatured collagen. The preferred raw material is corium derived from never-dried calf-hide or technical grades of collagen prepared from cowhide. The wet collagen source material such as corium is diced or chopped into small fragments of from one-fourth to one-half inch (6.4 mm. to 12.7 mm.) sizes in a cutting or grinding mill, such as, for example, an Urschel Mill. In the processing of corium into the fluffy fibers of the partial salt of collagen it is essential that the swelling or hydration of the collagen fibers be controlled. As stated in the aforementioned patents, if the swelling or hydration is excessive many more sites are produced for hydrogen bonding leading to an excessive hornification or densification upon drying. When hornification or densification occurs, the mechanical shredding or opening of the dried material will not produce the required low bulk density and fluffiness to impart the hemostatic-adhesive efficacy.

Accordingly, the processing of the corium or other collagen source material is effected in a liquid medium consisting of a major proportion of a water-miscible organic liquid with the balance water. For example, the collagen chips may first be slurried or mixed in a liquid consisting of 70% ethanol and 30% (by weight) water including the water contained in the wet chips. After separating excess liquid the recovered mass may be again slurried in a liquid containing a higher proportion of ethanol. In each successive slurrying operation the proportion of ethanol is increased. Several such steps are utilized until the amount of water is reduced to about 2%. The partial acid salt of collagen is formed by incorporating the required amount of an ionizable acid in the slurrying liquid in one of the slurrying steps. The amount of acid is such as to provide the collagen product with a bound acid content of from about 50 to 90%, preferably 60% to 85%, of the theoretical stoichiometric bound acid content.

Following the final slurrying step, excess liquid is removed as by centrifugation and drying. Drying may be effected either by oven drying or vacuum drying as at, for example, 40° C. under a 29 inch (736.6 mm.) vacuum for about 10 to 16 hours. In general, such vacuum drying will reduce the volatile content of the chips to under 1%. Prior to fiberization into the fluffy, fibrous product or the fluffing operation to produce fibers of the required size and into the fibrous product of the required bulk density, the dried material is preferably conditioned. The conditioning may be readily effected by allowing the material to remain at normal atmospheric temperatures and humidities (21° to 24° C., 40% to 60% R.H.) for from about 8 to 24 hours. The fiberization or fluffing operation may be effected by apparatus such as a hammer mill type comminution mill, for example, a Fitz Mill.

A measure of the fluffiness and a rough indication of a satisfactory fiber length distribution of the fibers is bulk density. The bulk density is measured by adding the fibrous collagen products as initially fluffed to a 100 ml. graduate cylinder without any compression step and determining the weight of the added 100 mls. of the product.

In forming the partial salt of collagen, hydrochloric acid is the preferred acid and is used in the examples which follow merely because it is relatively inexpensive and allows ready flexibility and ease of control. Other ionizable acids, both inorganic and ionizable organic acids, such as, for example, sulfuric acid, hydrobromic acid, phosphoric acid, cyanoacetic acid, acetic acid, citric acid, and lactic acid are satisfactory. Sulfuric acid, for example, is satisfactory, but control of the action is difficult. Citric acid may be substitued for hydrochloric acid with about equal results. "Ease of control" has reference to the ability to arrest the swelling and hydrolysis of the collagen fibers so as to prevent the rapid degradation of the material to a water-soluble product.

In the examples which follow, the fluffy, finely-divided fibrous collagen product was derived from wet or green bovine corium. The fluffy, fibrous collagen product was a water-insoluble, ionizable, partial hydrogen chloride salt of collagen containing approximately 84% of the theoretical stoichiometric bound acid content. The product was fiberized or fluffed by passing it through a Friz Mill (Model DA50-6-563) operated at 6250 rpm. equipped with a No. 4 screen having openings of 0.243 in. (6.2 mm.). It was then subjected to a second pass using a special slotted screen having openings 0.062 in. (1.6 mm.) × 0.5 in. (12.7 mm.) with the slots at an angle of 30° to the sides of the screen.

The bulk density of the fluffed, fibrous partial salt of collagen was 2.0 – 2.5 pounds per cubic foot (0.032 – 0.040 gm./cc.).

Upon disintegrating a sample of the fluffy, finely-divided fibrous material in water at a solids concentration of 0.5% by weight by subjecting the mixture to the action of a Waring Blendor at high speed for 30 minutes, a stable dispersion was formed having a pH of 3.20.

In the production of the liquid-laid, non-woven webs of the present invention, conventional apparatus such as used in the papermaking industry and in the production of non-woven webs may be used. The finely-divided, fibrous collagenous fibers are slurried in the water-miscible organic liquid by the use of a suitable mixing device such as a beater wherein the beater is used solely as a mixing device since the collagenous fibers do not require hydration or fibrillation. The slurry or furnish may contain from about 0.1 to about 3% of the collagenous fibers, preferably 0.3 to 0.5%, dry basis. The slurry or furnish is then passed to a suitable collecting screen where the collagenous fibers are sheeted or deposited. Fourdrinier, cylinder vat, Roto-former and other sheet forming devices are satisfactory. After removing the wet-laid sheet or web from the collecting screen, excess liquid is removed, the sheet pressed uniformly using a closely limited pressure of from about 0.1 to about 1.0 psi (7 to 70.3 gm./sq.cm.), preferably 0.3 to 0.5 psi (20 to 35 gm./sq.cm.), and then drying the sheet.

The following examples are illustrative of the present invention:

EXAMPLES I-VI

Physical properties of the hemostat-adhesive non-woven webs of the present invention were determined from handsheets prepared from slurries of the above described collagenous fibers in ethanol to which had been added concentrated hydrochloric acid. In the preparation of these handsheets a modified 8 inch × 8 inch (20.32 cm. ×20.32 cm.) Williams handsheet mold was utilized. The normal wire mesh screen at the bottom of the handsheet mold was covered with a polypropylene filter fabric consisting of a 2/2 twill weave structure, the fabric having a porosity of 85-90 CFM (240-255 l./min.) (Chicopee Polypropylene 6007010 fabric).

In each instance the ball valve located at the bottom of the handsheet mold's water leg was closed and acidified ethanol, about 4000 mls., poured through the polypropylene filter fabric to bring the level of the liquid to just cover the polypropylene filter fabric. For the preparation of handsheets of approximately 1.1 to 1.5 mm. thick (about 185 lbs. per 3000 sq. ft., 84 kg. per 279 sq. m or 300 gm. per sq.m.) 9.5 gms. of the fluffy, fibrous material was added to 3000 mls. of the ethanol to which had been added 3 drops (0.3 gm.) of concentrated hydrochloric acid (37.5% HCl) per 30 lbs. (13.62 kg.) of ethanol, forming a slurry of about 0.36% (dry basis) by weight of the fibers, and the slurry gently agitated for approximately 5 minutes. The slurry was poured immediately into the handsheet mold and the slurry agitated by lowering and raising a perforated plunger 3 times. The ball valve was then opened to allow most of the liquid to drain by hydrostatic pressure, usually requiring from about 20 to 30 seconds. About ½ to 1 inch (12 to 25 mm.) of liquid was allowed to remain over the polypropylene filter fabric. Thin areas or voids in the sheet on the filter fabric were filled in with suspended fibers by gently agitating the slurry with a spatula and moving fibers by gently agitating the slurry with a spatula and moving fibers to the thin areas or voids. When the sheet appeared to be quite uniform, the ball valve was opened completely and all liquid allowed to drain.

The mold was opened and the formed wet, non-woven web was covered with a polypropylene filter fabric (Chicopee Polypropylene 6007010 fabric) to form a sandwiched web between the lower and upper filter fabrics. Because of a gasket between the base of the sheet mold and the upper hinged chamber, the effective web forming surface of the sheet mold is approximately 7,625 in. × 7.625 in. (19.37 cm. × 19.37 cm.). A taffeta weave polyethylene terephthalate (Dacron) pouch containing five sheets 8 in. × 8 in. × 26 mil [20.32 cm. × 20.32 cm. ×0.66 mm.] of dry blotting paper was placed over the upper polypropylene filter fabric. Using a rubber photographic print roller, the assembly was manually rolled twice using light pressure, the rolling starting at each of the four sides and extending to the center of the web. The polyethylene terephthalate pouch was then placed on a table and the sandwiched web removed from the mold and placed on the pouch with the lower filter fabric of the "sandwich" contracting the pouch. This assembly was manually rolled once using light pressure, the rolling starting at each of the sides and extending to the center of the web.

The web was gently removed by peeling away the upper and lower filter fabrics and placed between polyethylene terephthalate (Mylar) films. The assembly was manually rolled using gentle pressure starting at each side and extending to the center of the web to equalize the thickness of the web. The web between the polyethylene terphthalate films was stored in a polyethylene bag until six such webs were produced. The films of each sandwich were replaced with a polypropylene filter fabric and the six webs between the filter fabrics were stacked. The stack was subjected to compression at a pressure of approximately 0.3 – 0.4 psi (21 – 28.1 gm./sq. cm.) of web area for about 10 minutes. Since the available freeze dryer was provided with 4 trays, each accommodating 6 webs, the pressed webs were stored in a polyethylene bag. The foregoing procedure was repeated until a total of 24 webs had been prepared.

Upon completion of such series of webs, the upper polypropylene filter fabric of each sandwich web was replaced with a polyethylene terephthalate film. The sandwich web was then placed in a freeze dryer tray with the Mylar film down and the covering polypropylene filter fabric removed. As each tray was loaded with 6 webs it was inserted on a shelf in the freeze dryer. Freeze drying was effeccted by placing the tray in a Repp Freeze Drier, Model 40. The drying conditions utilized an initial shelf temperature of about −40° C. maintained for about 30 minutes without application of a vacuum. The apparatus was then set for condenser refrigeration until the condenser temperature was lowered to about −40° C. which in general required about 2 minutes. Vacuum was then applied to reduce the pressure to about 100 microns. Heating of the tray was initiated to raise the shelf temperature to 35° – 38° C. in a 2 hour period and the condenser temperature lowered to about −60° C. The vacuum was reduced to 5 to 20 microns and these conditions maintained for 14 to 16 hours.

Upon completion of the freeze drying period, the webs were removed and the thickness of each web measured at 4 different area per web, the web being sandwiched between polyethylene terephthalate (Mylar) films. Freeze drying results in a shrinkage of the webs to approximately 7 in. × 7 in. (17.78 cm. × 17.78 cm.). The webs were then trimmed to approximately 6.125 in. × 6.125 in. (15.56 cm. × 15.56 cm.) and 3 trimmed webs selected at random from the series were weighed. All webs were placed on polyethylene terephthalate films and placed on racks in an air circulating oven, temperature 105° C., for 2 hours. The webs were then placed in a dessicator with anhydrous calcium sulfate (Drierite) and cooled to room temperature. Following cooling, one web was selected at random for physical testing and the remaining 23 webs placed in a polyethylene bag and the bag sealed. The sealed bag was placed in a second polyethylene bag and sealed. The sealed packages from a number of series were shipped by parcel post over a distance of about 2,000 miles (3,220 km.). All samples withstood handling and shipping without crumbling or disintegrating. Samples were subsequently used in "in vivo" animal testing.

Trimmings from the original webs were selected at random and small samples were dispersed at 0.5% solids in distilled water in a Waring Blendor at high speed for 30 minutes. The resulting dispersions had a pH of 3.22 which was substantially identical to the pH of like dispersions formed from the original fibers.

The average density in grams per cubic centimeter was calculated from the average weight of three webs and the average measured caliper and area of the webs. The measurements and density for several series of webs are reported in Table 1.

The water holding capacity of the webs was determined by accurately weighing 1.00 gram samples of webs and placing a sample on a 7 in. × 7 in. (17.75 cm. × 17.75 cm.) piece of cheesecloth. The corners of the cheesecloth were brought together and stapled to form a "basket." The basket was immersed in distilled water by means of forceps and maintained submerged in the water for 60 seconds. The basket was then removed and the excess water allowed to drain without shaking for 60 seconds. The wet basket and contained web were immediately weighed. The same procedure was used to determine the water holding capacity of a like piece of cheesecloth and staple. From the determined weights, the water holding capacity of the webs was calculated and is reported in Table 1 as grams of water per gram of web.

Samples of the sheets were also subjected to a bursting test in accordance with TAPPI Standard Test Method T403 ts-63 using a Mullen Burst Tester. The Burst as reported in Table 1 was the average of the pressure in psi (gm./sq. cm.) required to burst the samples.

Samples of the sheets were subjected to a tear test in accordance with TAPPI Standard Test Method T220 m-60 using an Elmendorf Tear Tester. The Tear as reported in Table 1 was the average force in grams to cause a tear in the sheet to progress.

Non-woven webs or sheets formed according to the present method are readily distinguishable from those formed in accordance with the method described in U.S. Patent No. 3,810,473. An "in vitro" test differentiates the overall compactness and fiber-to-fiber bonding in the web and illustrates the adverse effect attributable to the higher proportions of water present in the fiber slurry or furnish used in preparing the webs. The test which may be termed a "Disintegration Test" is a qualitative test for the looseness of the web structure.

This test is preformed by the use of a 0.9% saline solution maintained at 25° ±0.5° C. Samples of the non-woven web are cut by the use of a sharp bladed paper cutter to a 1 in. × 1 in. (2.54 cm. × 2.54 cm.) size. About 250 ml. of the saline solution is poured into a container such as a Petri dish [4 in. (10.16 cm.) diameter, 2 in. (5.08 cm.) height] and allowed to stand for about 5 minutes to eliminate turbulence. A 1 in. × 1 in. (2.54 cm. × 2.54 cm.) sample is placed on a wire cloth support [19 guage wire, 0.5 in. (1.27 cm.) opening] and the support gently lowered into the saline solution, thereby allowing the sample to float on the surface of the solution. The wetting time is the time in seconds required to completely wet the web; that is, a complete disappearance of white colored areas. The disintegration time is the time in seconds required for the loss of the web structure. The time of disintegration consists of the wetting time and the time required for the loss of the web structure.

Samples of the freeze dried webs of Examples III, IV, V and VI and sample of freeze dried webs prepared from slurries of the hemostat-adhesive fibers in mixtures of 95% ethanol and 5% water (by volume) and 90% ethanol and 10% water (by volume) were heated at 105° C. for 2 hours in an air circulating oven. The webs formed from the 95/5 and 90/10 ethanol/water slurries were prepared as described in U.S. Pat. No. 3,810,743. All samples, after heat treatment, contained between 3.2% and 7.5% moisture, by weight. A series of samples were also conditioned after the heat treatment by maintaining the samples in air at a temperature of 72° F. (22.2° C.) and a relative humidity of 50% for 7 hours. The conditioned samples contained between 11.3% and 11.7% moisture, by weight.

A minimum of 5 samples of each of the webs so prepared and treated were subjected to the Disintegration Test, the data being presented in Table 2.

The sensitivity of the webs to compactness and fiber-to-fiber bonding is illustrated by the disintegration time as related to the method of cutting webs from a sheet of the hemostat-adhesive fibers. Samples were cut from freeze dried webs of Examples III, IV, V and VI, after heating at 105° C. for 2 hours followed by conditioning, as described. One set of samples was cut using a sharp bladed paper cutter and a second set of samples was cut using a sharp razor blade. Visual inspection shows that samples cut using the paper cutter exhibit somewhat compressed edges as compared to the samples cut using a sharp razor blade. This slight compression is reflected in the results of the disintegration test as reported in Table 3.

When the samples cut with paper cutter were placed on the saline solution, the compacted edges separated from the bulk of the web appearing as thin strips or lines and required longer times for complete dispersion into the fibers. Samples cut using the razor blade do not exhibit a compaction of the edges and the fibers along the edges begin to separate and disperse almost instantaneously as the samples contact the saline solution.

These data presented in Tables 2 and 3 illustrate clearly that the webs prepared from slurries containing not more than about 2 to 5% water, at the most, are significantly more porous and absorbent and posses a significantly looser structure than webs prepared from slurries containing 5% and more water. The higher proportions of water increase the swelling of the fibers and the fibers become limp allowing them to drape over each and become entangled during sheet formation thus producing a more compacted structure and stiffer web and a web having a less absorbent structure. While the greater compaction results in a more coherent structure, it effects a significant loss in absorbency as reflected in the disintegration test. Although webs formed by the use of slurries containing the higher proportions of water show a satisfactory wetting time, the fibers of the webs do not self-disperse when the webs are placed and maintained in the saline solution.

Webs prepared according to the present method posses a minimum compaction with a minimum of fiber entanglement and hence there is no opportunity for densification. In the slurry containing the minimum of water, the fibers are stiff rather than limp, bend a minimal amount during sheet formation. Because of the very low compaction and low degree of fiber entanglement in the web structure, the web functions much like bulk fibers and effects a more rapid formation of an adhesive bond to the flesh surrounding the wound.

As shown in Table 2, the wetting times do not correspond to the disintegration times. Upon introducing the webs of the present method into the saline solution, the fibers in the marginal edge portions begin to separate from the bulk of the web and self-disperse in the saline solution almost instantaneously and before the web has been fully wet. In most instances, the webs have completely disintegrated before the web has been fully wetted. The data illustrate that when the web is formed from slurries containing 5% or more water, the web shows poor disintegration after 5 minutes and does not completely disintegrate after a long period.

The data presented in Table 3 illustrates the criticality of processing the webs. A mere slight compaction on the edges of the webs results in almost a doubling of the time of disintegration. As stated hereinbefore, in forming the webs or sheets, the webs or sheet prior to drying must be pressed under a pressure of between about 0.1 and about 1.0 psi (7 to 70.31 gm./sq.cm.). Such pressing imparts to the webs or sheets a sufficient cohesiveness to provide a product which is highly absorbent, flexible, non-flaking and can be handled and transported without separation of individual fibers.

Non-woven webs prepared as described hereinbefore were employed in a surgical test procedure designed to evaluate not only the efficacy of the webs as a hemostat and adhesive for several biological surfaces in warm blooded animal when wet with blood, but also to assess handling and delamination characteristics. "Severed" biological surfaces for the purpose of this invention includes cut, sliced, ripped, torn, abraded, punctured, burned, and tissue severed by any means or method whereby a fresh biological surface is present. Biological surfaces include tissue, cartilage, vessels, bone and other normal parts of a warm blooded animal that may require mending or joining.

In the surgical procedure the handling characteristics and the delamination characteristics were noted. The handling characteristics involved the cohesiveness, non-friability and stiffness of the webs. The delamination property involves the ability to remove excess marginal portions of the web without overcoming the adhesiveness of the portion of the web at the wound and without permitting a resumption of bleeding. Delamination is highly desirable so that in internal surgical procedures only so much of the material is allowed to remain as to effect hemostasis and seal the wound and permits the removal of excess material.

Prior to the use of webs in "in vivo" procedures the webs were removed from the polythylene bags for sterlization. The webs were first dried by heating in an air oven at 110° C. for 2 hours. The temperature was then raised to about 126° C. and maintained at that temperature for 20 hours. Such sterilization procedure results in a shrinkage of the webs to approximately 5.9375 in. × 5.9375 in. (15.08 cm. × 15.08 cm.).

The "in vivo" surgical procedures were carried out on anaesthetized mongrel dogs. The spleen of the dog was exposed and excised wounds were made, the wounds measured about 20 mm. × 10 mm. with a depth of about 1 to 2 mm. Swatches were cut from sample webs prepared as described above, the swatches being about 28 to 30 mm. × 18 to 20 mm. so as to overlap the wound 4 to 5 mm. on all sides. The investigators were provided with the sample webs without a knowledge of the history of the samples so that all evaluation was "blind."

A wound was swabbed with a dry, surgical cotton gauze pad so as to provide a freely bleeding wound and a swatch immediately placed over the wound. The swatch was held in place by the application of pressure with a dry cotton gauze pad. The pressure was applied for 60 seconds and the pad lifted to determine whether hemostasis had been effected. In those instances where hemostasis had not been effected the pad was again applied for 60 second intervals until hemostasis was effected.

Delamination was determined after the swatch had been on the wound for 20 to 25 minutes. In this determination, excess material was removed by grasping the overlapping edges of the swatch with forceps and lifting the free edges. The adhesion of the material to the wound surface and the ease of the removal of the material in excess of that required to prevent rebleeding of the wound was noted. The handling characteristics included a consideration of the physical properties of the webs such as cohesiveness and flakiness of the webs, the friability, the stiffness and ability of the web to conform to the wound surface and the abiltiy to cut swatches of a required size form the sheet with scissors to form clean cut edges.

The investigators' evaluation of the various webs is set forth in Table 4. The investigators rated the hemostatic, adhesive, handling and delamination properties using an arbitrary scale of 1 to 5. On this scale, 1 represents — Excellent; 2 — Excellent to Good; 3 — Good to Fair; 4 — Fair to Poor; and, 5 — Poor. A rating of 1 indicates a satisfactory characteristic; 2 indicates an acceptable characteristic; 3 indicates a questionable acceptability; 4 and 5 designate an unacceptable characteristic. Where one of the property ratings is 4 or 5, the web is considered unacceptable.

The fluffy, finely-divided fibrous collagen product utilized in forming the webs of the present invention was essentially identical to that of Example X of U.S. Pat. No. 3,742,955. As shown by the "in vivo" testing of the fibrous collagen product in the fluffy, finely-divided state on spleen wounds, the time required to effect hemostasis was from 2.5 to 3 minutes. As compared to the time required for hemostasis when webs of the present invention are used (1 minute), this longer time is not serious. The adhesion of the fluffy, fibrous product is excellent to good. Delamination is likewise excellent to good but requires grasping of groups of protruding fibers. The handling characteristics of the fluffy, fibrous product are extremely poor because of its relatively large bulk as compared to the compactness of the fibers in a web form. Further, it is difficult to confine the fibers in delivering a wad to a wound site. Upon grasping a wad and removing it from the bulk of the fluffy, fibrous product, only the fibers compressed between the forceps of finger tips are held firmly. Many fine fibers will extend from the compressed mass but are only loosely held in the wad by fiber-to-fiber friction and entanglement and are easily dislodged. A rapid movement of the grasped wad through the air results in a large number of the loosely held fibers to become detached and float in the air.

In the bulk form as disclosed in U.S. Pat. No. 3,742,955, the fibers are very loosely associated whereas in the web forms as described in U.S. Pat. No. 3,810,473 and in this application the fibers are closely associated and compacted in a random arrangement. Accordingly, the fibers in a web form are more rapidly wetted and thereby effect hemostasis and adhesion more rapidly. Also, there is a more uniform wetting of the closely associated fibers due to the structure of the web as compared to a bulk mass of fibers. This is shown clearly by the data included in Table 4.

The web as formed pursuant to the present method involves a carefully controlled pressing prior to freeze drying. Also, since in sheeting the fibers there is present a very minimum amount of water, the fibers are less flexible, a condition which does not favor fiber entanglement, as compared to sheeting the fibers in the presence of greater amounts of water. In the present method the fibers are laid down upon each other in a random arrangement. The controlled, limited pressure while the mat is wet with alcohol and the very small proportion of water is sufficient to bring the randomly arranged fibers into a fiber to fiber contact and to distribute uniformly the liquid throughout the web. This mild pressing imparts sufficient strength to form a coherent structure offering a minimal resistance to a wetting and dispersion of the fibers upon placing the web on a liquid such as a saline solution. This is shown by the data in Tables 2 and 3.

Because of the very small proportion of water present in the dispersing liquid, there is substantially no swelling of the fibers during heet formation and, hence, a very minimal densification or hornification of the fibers during drying. Since there is substantially no swelling of the fibers, there is no opportunity for fiber to fiber bonding upon drying. In forming webs in accordance with U.S. Pat. No. 3,810,473 where at least 5%, by volume, of water is present, the fibers become partially swollen and some densification results on drying. The flexibility of the fibers causes a greater entanglement during sheet formation and the swelling of the fibers by the water results in a greater fiber to fiber bonding during drying. Hence, as shown by the data in Table 2, upon placing a web on a liquid such as a saline solution, the web will swell but does not completely disintegrate. On the other hand, when webs of the present invention are placed on a saline solution, the web swells, the fibers separate and begin to self-disperse almost instantaneously and the web disintegrates completely in a brief period.

The presence of the greater proportion of water in the dispersing liquid causes a swelling of the fibers and results in a greater fiber to fiber bonding to form a more coherent structure, but thereby effects an appreciable loss in absorbency. The increased coherency and the loss in absorbency is illustrated in Table 2 as reflected in the failure of the webs (Samples 95/5 and 90/10 ) to disintergrate in the saline solution. The increased fiber to fiber bonding is also apparent from the results of the "in vivo" procedure. Although the hemostatic, adhesive and handling characteristics are satisfactory, the delamination property illustrates the greater coherency in structure resulting from a stronger fiber to fiber bonding as illustrated by Samples B and C, Table 4.

The delamination property of the present webs is highly advantageous so that only a minimum of the hemostatic material remains after repair of an internal wound. This delamination property permits a ready removal of all excess portions of the web without a breakthrough bleeding. The only portion of the web remaining is that portion which effected hemostasis and sealed the wound.

In the foregoing discussion it is stated that in the preparation of the slurrying liquid, 0,3 gm. of concentrated hydrochloric acid (37.5% HCl) is added to 13.62 kg. of ethanol. The specific amount of added acid will vary directly with the proportion of fiber to be slurried in the ethanol. The fluffy fibers include some free hydrogen chloride and the purpose of the addition of the acid to the slurrying liquid is to prevent a leaching of hydrogen chloride from the fibers by the large volume or liquid. The specific amount of added acid should be sufficient to maintain the total acid content of the sheeted fibers equivalent to that of the initial fibers. The simplest and most ready method of comparing the acid content of the sheeted fibers with that of the initial fibers is to form 0.5% dispersions in water and measuring the pH of the dispersions as described hereinbefore. Reference is made to the addition of hydrochloric acid because the fibers consist of a partial hydrogen chloride salt of collagen. It is to be understood that the specific acid used would be dependent upon the acid employed in forming the partial salt of collagen.

From the foregoing description it is apparent that the present invention provides a liquid-laid, non-woven, hemostatadhesive, web dressing for severed biological surfaces formed of hemostat-adhesive fibers consisting of an ionizable, waterinsoluble, partial salt of collagen, the partial salt of collagen containing from about 50 to 90%, preferably about 84%, of the theoretical stoichiometric amount of ionizable acid, preferably hydrochloric acid, the web having a water holding capacity of from about 20 gm. to about 25 gm. per gram of web, based upon a basis weight of about 300 gm. per sq. m. and being further characterized in that when placed on a 0.9% saline solution disintegrated completely and the fibers self disperse immediately upon contacting the solution.

As described, the web dressings are formed from hemostatadhesive fibers that consist of an ionizable, water-insoluble, partial cid salt of collagen, preferably a partial hydrogen chloride salt, a mass of the fibers having a bulk density of not more than 8 poinds per cubic foot (0.128 gm.cc/) preferably between 0.024 and 0.096 gm. per cc. The fibers are slurried at a concentration of from 0.1 to 3%, preferably about 0.3 to 0.5%, dry basis, in a water-miscible organic liquid, preferably ethanol, containing a small proportion of an ionizable acid, preferably hydrochloric acid, the amount of acid being sufficient to prevent leaching of the acid from the partial salt, preferably 0.3 gm. of concentrated hydrochloric acid (37.5% HCL) per 13.62 kg. of ethanol, based upon a fiber concentration of 0.3 to 0.5%, sheeting the fibers to form a web, removing excess liquid from the web, subjecting the web to a uniform pressure between 0.1 to 1.0 psi (7 and 70.3 gm. per sq. cm.), preferably 0.3 to 0.5 psi (20 to 35 gm. per sq. cm.) and freeze drying the web.

TABLE 1

| Sample | I | II | III | IV | V | VI |
|---|---|---|---|---|---|---|
| Weight, gm. | 7.22 | 7.18 | 7.64 | 7.83 | 7.51 | 7.35 |
| Thickness, mm | 1.40 | 1.35 | 1.35 | 1.38 | 1.38 | 1.36 |
| Area, $cm^2$ | 237 | 237 | 242 | 242 | 242 | 242 |
| Volume, $cm^3$ | 33.2 | 32.0 | 32.7 | 33.4 | 33.4 | 32.9 |
| Basis Wt. $gm/m^2$ | 305 | 303 | 316 | 323 | 310 | 304 |
| Density, $gm/cm^3$ | 0.22 | 0.22 | 0.23 | 0.23 | 0.23 | 0.22 |
| Water Holding Capacity | 22 | 22 | 20 | 22 | 22 | 23 |
| Burst, psi | 3 | 3 | 3 | 3.5 | 4 | 4 |
| (gm./sq.cm.) | (211) | (211) | (211) | (246) | (281) | (281) |
| Tear, gm. | 8 | 8 | 8 | 8 | 8 | 8 |

TABLE 2

| Sample | Web Treatment | Moisture % | Wetting Time (sec.) | Disintegration Time (sec.) | Remarks |
|---|---|---|---|---|---|
| III | 105° C–2 hrs. | 3.8 | 4–7 | 2–10 | Swells - accompanied by complete dispersion into fibers |
| III | conditioned | 11.6 | 4–10 | 2–18 | '' |
| IV | 105° C–2 hrs. | 4.6 | 6–8 | 2–9 | '' |
| IV | conditioned | 11.3 | 2–9 | 2–22 | '' |
| V | 105° C–2 hrs. | 3.5 | 5–9 | 2–9 | '' |
| V | conditioned | 11.3 | 6–9 | 3–20 | '' |
| VI | 105° C–2 hrs. | 3.2 | 5–8 | 2–9 | '' |
| VI | conditioned | 11.4 | 5–8 | 2–18 | '' |
| 95/5 | 105° C–2 hrs. | 5.75 | 10–14 | — | Swells; very little disintegration, not complete |
| 95/5 | conditioned | 11.7 | 4–10 | — | '' |
| 90/10 | 105° C–2 hrs. | 7.5 | 1–3 | — | Swells; no disintegration in one week |
| 90/10 | conditioned | 11.1 | 5–10 | — | '' |

TABLE 3

| Sample | Moisture % | Type of Cutter | Disintegration Time (sec.) |
|---|---|---|---|
| III | 11.6 | Paper Cutter | 3–13 |
| III | 11.6 | Razor Blade | 3–8 |
| IV | 11.3 | Paper Cutter | 2–17 |
| IV | 11.3 | Razor Blade | 3–10 |
| V | 11.3 | Paper Cutter | 3–14 |
| V | 11.3 | Razor Blade | 3–9 |
| VI | 11.4 | Paper Cutter | 2–14 |
| VI | 11.4 | Razor Blade | 3–6 |

TABLE 4

| Sample | Rating | | | |
|---|---|---|---|---|
| | Hemostat | Adhesive | Handling | Delamination |
| A | 1 | 1 | 2 | 1 |
| I | 1 | 2 | 3 | 1 |
| II | 1 | 1 | 3 | 1 |
| B | 1 | 1 | 2 | 4–5* |
| C | 1 | 1 | — | 3 |
| D | 3 | 2 | 5 | 2 |

Sample A prepared as described in Examples 1 – VI.
Samples I and II, Examples I and II.
Samples B and C prepared from slurries in 95/5 ethanol/water mixture as described in Sample A-2 in U.S. Patent No. 3,810,473.
Sample D fluffy, finely-divided fibrous product substantially identical to Example X of U.S. Patent No. 3,742,955. Rating Scale: 1 — Excellent, 2 — Good, 3 — Good-Fair, 4 — Fair-Poor, 5 — Poor.
*— Two sites good; two sites poor; two sites breakthrough bleeding; two sites entire sample removed.

What is claimed is:

1. The method of forming a hemostat-adhesive, liquid-laid, non-woven web dressing for severed biological surfaces from hemostat-adhesive fibers consisting of an ionizable, water-insoluble, partial acid salt of collagen, the partial acid salt of collagen containing from about 50 to 90% of the theoretical stoichiometric amount of ionizable acid, the steps of preparing a slurry of the fibers in a water-miscible organic liquid containing a small proportion of an ionizable acid, the proportion of acid being sufficient to prevent leaching of acid from the partial salt of collagen, sheeting the fibers to form a web, removing excess liquid from the web, subjecting the web to a uniform pressure between 7 and 70,3 gm. per sq. cm. and thereafter freeze drying the web.

2. The method as defined in claim 1 wherein the fibers consist of a partial hydrogen chloride salt of collagen and the ionizable acid is hydrochloric acid.

3. The method as defined in claim 1 wherein the organic liquid is ethanol and contains not more than 5% water.

4. The method as defined in claim 1 wherein the fibers consist of a partial hydrogen chloride salt of collagen, the organic liquid is ethanol and contains not more than 5% water and the ionizable acid is hydrochloric acid.

5. The method as defined in claim 1 wherein the fibers consist of a partial hydrogen chloride salt of collagen containing about 84% of the theoretical stoichiometric amount of hydrogen chloride, the organic liquid is ethanol, the ionizable acid is hydrochloric acid in an amount of about 0.3 gm. of concentrated hydrochloric acid (37.5% of HCL) per 13.62 kg. of ethanol based upon a fiber concentration of 0.3% to 0.5%, dry basis and the web is subjected to a pressure of 20 to 35 gm./sq. cm.

6. A hemostat-adhesive web dressing for severed biological surfaces comprising a liquid-laid, non-woven web having hemostat-adhesive properties and formed of hemostatic-adhesive fibers consisting of an ionizable, water-insoluble, partial salt of collagen, the web having a water holding capacity of from about 20 to about 25 gm. of water per gm. of web, based upon a basis weight of about 300 gm. per sq. m., and being further characterized in that when placed on a 0.9% saline solution disintegrates completely and the fibers self disperse immediately upon contacting the solution, the partial salt of collagen containing from about 50 to 90% of the theoretical stoichiometric amount of ionizable acid.

7. The hemostat-adhesive web dressing as deined in claim 6 wherin the fibers consist of a partial hydrogen chloride salt of collagen.

8. The hemostat-adhesive web dressing as defined in claim 6 wherein the fibers consist of a partial hydrogen chloride salt of collagen containing from 50% to 90% of the theoretical stoichiometric amount of hydrogen chloride.

9. The hemostat-adhesive web dressing as defined in claim 6 wherein the fibers consist of a partial hydrogen chloride salt of collagen containing about 84% of the theoretical stoichiometric amount of hydrogen chloride.

* * * * *

UNITED STATES PATENT OFFICE
CERTIFICATE OF CORRECTION

PATENT NO. : 4,016,877
DATED : April 12, 1977
INVENTOR(S) : Mamerto M. Cruz, Jr., John H. Tenery and LaVerne C. Tressler It is certified that error appears in the above-identified patent and that said Letters Patent are hereby corrected as shown below:

Column 1, line 21, "several" should read --severed--; column 1, line 28, "hemostatadhesive" should read --hemostat-adhesive--. Column 2, line 17, "liquidlaid" should read --liquid-laid--; column 2, line 24, "5" should read --5%--; column 2, line 58, "hemostatadhesive" should read --hemostat-adhesive--. Column 4, line 54, "Friz" should read --Fitz--; column 4, line 54, "(Model DA50-6-563)" should read --(Model DA50-6-5634)--. Column 6, line 6, "7,625" should read --7.625--; column 6, line 18, "contracting" should read --contacting--; column 6, line 28, "terphthalate" should read --terephthalate--; column 6, line 47, "effeccted" should read --effected--; column 6, line 63, "area" should read --areas--. Column 8, line 16, "sample" should read --samples--; column 8, line 47, "with paper" should read --with the paper--; column 8, line 58, "posses" should read --possess--. Column 9, line 41, "several" should read --severed--; column 9, line 41, "in warm" should read --in a warm--. Column 10, line 35, "abiltiy" should read --ability--; column 10, line 68, "forceps of finger" should read --forceps or finger--. Column 11, line 39, "heet" should read --sheet--. Column 12, line 14, "0,3" should read --0.3--; column 12, line 22, "or" should read --of--; column 12, line 36, "hemostatadhesive" should read

UNITED STATES PATENT OFFICE
CERTIFICATE OF CORRECTION

PATENT NO. : 4,016,877
DATED : April 12, 1977
INVENTOR(S) : Mamerto M. Cruz, Jr., John H. Tenery and LaVerne C. Tressler It is certified that error appears in the above-identified patent and that said Letters Patent are hereby corrected as shown below:

--hemostat-adhesive--; column 12, line 50, "hemostatadhesive" should read --hemostat-adhesive--; column 12, line 51, "cid" should read --acid--; column 12, line 53, "poinds" should read --pounds--; column 12, line 54 "(0.128 gm.ccl)" should read --(0.128 gm./cc.)--; column 12, line 62, "(37.5% HCL)" should read --(37.5% HCl)--. Column 14, line 37, Claim 1, "70,3" should read --70.3--; column 14, line 56, Claim 5, "(37.5% of HCL)" should read --(37.5% of HCl)--. Column 15, line 6, Claim 7, "deined" should read --defined--; column 15, line 7, Claim 7, "wherin" should read --wherein--.

Signed and Sealed this

Eighteenth Day of October 1977

[SEAL]

Attest:

RUTH C. MASON
Attesting Officer

LUTRELLE F. PARKER
Acting Commissioner of Patents and Trademarks